(12) United States Patent  (10) Patent No.: US 8,328,458 B2
Werth  (45) Date of Patent: *Dec. 11, 2012

(54) SANITARY CLAMP (75) Inventor: Albert A. Werth, Kewadin, MI (US)

(73) Assignee: Twin Bay Medical, Inc., Williamsburg, MI (US)

( * ) Notice: Subject to any disclaimer, the term of this patent is extended or adjusted under 35 U.S.C. 154(b) by 245 days.

This patent is subject to a terminal disclaimer.

(21) Appl. No.: 12/432,370

(22) Filed: Apr. 29, 2009

(65) Prior Publication Data

US 2009/0208277 A1 Aug. 20, 2009

Related U.S. Application Data (63) Continuation-in-part of application No. 12/175,712, filed on Jul. 18, 2008.

(60) Provisional application No. 60/950,968, filed on Jul. 20, 2007.

(51) Int. Cl.
 B25G 3/24 (2006.01)
 F16B 2/02 (2006.01)
 F16B 7/04 (2006.01)

(52) U.S. Cl. ........ 403/289; 403/290; 403/313; 285/415; 24/16 R (58) Field of Classification Search .......... 403/110, 403/289, 290, 312–314; 285/407, 412, 410, 285/411, 414, 415, 420, 406, 409, 364, 366, 285/368, 373, 419; 411/182, 580, 388; 24/16 R, 24/20 R, 284, 285; 248/62, 74.1, 230.1, 248/229.13, 229.23

See application file for complete search history.

(56) References Cited

U.S. PATENT DOCUMENTS

| 850,731 | A |   | 4/1907 | Christensen et al. |
| 1,441,154 | A | * | 1/1923 | Johnson ........................ 24/20 R |
| 3,860,997 | A | * | 1/1975 | Van Riper et al. .......... 24/16 PB |
| 3,915,167 | A |   | 10/1975 | Waterman |
| 4,049,301 | A |   | 9/1977 | Schenk |
| 4,212,303 | A |   | 7/1980 | Nolan |
| 4,247,076 | A |   | 1/1981 | Larkin |
| 4,442,994 | A |   | 4/1984 | Logsdon |
| 4,487,205 | A |   | 12/1984 | Di Giovanni et al. |
| 4,557,024 | A | * | 12/1985 | Roberts et al. .............. 24/20 TT |
| 4,588,160 | A |   | 5/1986 | Flynn et al. |
| 4,736,925 | A |   | 4/1988 | Kamstrup-Larsen et al. |

(Continued)

OTHER PUBLICATIONS

Notification of Transmittal, International Search Report and Written Opinion dated Dec. 29, 2010 from the corresponding International Application No. PCT/US2010/032670 filed Apr. 28, 2010.

(Continued)

Primary Examiner — Michael P Ferguson
Assistant Examiner — Eric Chau
(74) Attorney, Agent, or Firm — Young Basile (57) ABSTRACT A sanitary clamp for connection to a pair of barb connectors each having one end terminating at a funnel shaped portion is described herein. The sanitary clamp includes a first member having a first semi-circular center portion disposed between a first end and a second end. A second member has a second semi-circular center portion disposed between a first end and a second end. Said first ends of the first and second members are configured to pivotally connect to each other, and said second ends of the first and second members include a locking mechanism for selectively locking the second ends of the first and second members in engagement.

23 Claims, 6 Drawing Sheets

U.S. PATENT DOCUMENTS

| | | | |
|---|---|---|---|
| 4,942,886 A | 7/1990 | Timmons | |
| 4,944,485 A | 7/1990 | Daoud et al. | |
| 5,203,056 A | 4/1993 | Funk et al. | |
| 5,238,218 A | 8/1993 | Mackal | |
| 5,271,649 A | 12/1993 | Gromotka | |
| 5,305,978 A * | 4/1994 | Current | 248/230.4 |
| 5,318,546 A | 6/1994 | Bierman | |
| 5,590,859 A | 1/1997 | Lord | |
| 5,653,481 A * | 8/1997 | Alderman | 285/363 |
| 5,676,676 A | 10/1997 | Porter | |
| 5,697,942 A | 12/1997 | Palti | |
| 5,713,912 A | 2/1998 | Porter | |
| 5,729,872 A | 3/1998 | Ginocchio | |
| 6,101,684 A | 8/2000 | Ginocchio | |
| 6,113,062 A | 9/2000 | Schnell et al. | |
| 6,173,926 B1 | 1/2001 | Elvegaard | |
| 6,234,448 B1 | 5/2001 | Porat | |
| 6,261,254 B1 | 7/2001 | Baron et al. | |
| 6,390,721 B1 | 5/2002 | Wilson, II et al. | |
| 6,422,529 B1 | 7/2002 | Adelberg | |
| 6,523,866 B2 * | 2/2003 | Lin | 285/410 |
| 6,644,618 B1 | 11/2003 | Balboa | |
| 6,676,091 B2 | 1/2004 | Hauer | |
| 6,679,529 B2 | 1/2004 | Johnson et al. | |
| 6,708,377 B2 * | 3/2004 | Maunder | 24/279 |
| 6,755,445 B2 * | 6/2004 | Balamuta et al. | 285/357 |
| 6,796,586 B2 | 9/2004 | Werth | |
| 7,284,137 B2 | 10/2007 | Clark et al. | |
| 7,284,731 B1 * | 10/2007 | Johnson et al. | 248/74.4 |
| 7,650,767 B2 * | 1/2010 | Robinson | 70/34 |
| 7,677,612 B2 * | 3/2010 | Maunder | 285/411 |
| 7,740,211 B2 * | 6/2010 | Dukes | 248/74.4 |
| 7,744,624 B2 | 6/2010 | Bettuchi | |
| 7,883,121 B2 * | 2/2011 | Henry | 285/410 |
| 2003/0188401 A1 | 10/2003 | Huang | |
| 2004/0045447 A1 * | 3/2004 | Navarro | 99/403 |
| 2005/0258648 A1 * | 11/2005 | Newman | 285/364 |
| 2006/0131465 A1 | 6/2006 | Lynch, Jr. et al. | |
| 2006/0272369 A1 * | 12/2006 | Stachowiak, Jr. | 70/164 |
| 2008/0125811 A1 | 5/2008 | Bettuchi | |

OTHER PUBLICATIONS

Written Opinion of the International Searching Authority and International Search Report dated Sep. 3, 2009 from a related application, International Application No. PCT/US2009/032230 filed Jan. 28, 2009.

* cited by examiner

SANITARY CLAMP

RELATED APPLICATIONS

This application is a continuation-in-part application of pending U.S. patent application Ser. No. 12/175,712 filed on Jul. 18, 2008, which claims priority of U.S. Provisional Patent Application Ser. No. 60/950,968 filed on Jul. 20, 2007, both of which are incorporated herein by reference in their entirety.

FIELD OF THE INVENTION

The invention relates to a disposable sanitary clamp for holding a pair of sanitary connections together.

BACKGROUND

Flexible tubing made of plastic or rubber is widely used in the medical, pharmaceutical, biopharmaceutical, food and beverage and other laboratory environments. For certain assemblies involving connections from a medical instrument to a patient, stainless steel connectors or clamps have been used to connect ends of the flexible tubing together. Stainless steel connectors or clamps have the advantage of being capable of sterilization and therefore being reusable. However, stainless steel connectors are expensive to manufacture and do not completely protect against cross contamination.

It would be advantageous to provide a connector or clamp which is manufactured of a material that is resistant to solvents, acids, bases and heat and which is capable of use in applications requiring purity of the material. It would be advantageous to provide a clamp that is for a single use only and that is disposable to eliminate potential cross contamination while providing superior sealing and/or connection for the flexible tubing.

SUMMARY

Examples of sanitary clamps as described herein can address the aforementioned concerns as related to a clamp for connecting sections of flexible tubing having funnel shaped barb connectors at their ends.

In one example, a sanitary clamp is provided for connection to a pair of barb connectors each having an end terminating at a funnel shaped portion. The sanitary clamp is made of a high molecular thermoplastic polymer to provide a cost efficient disposable clamp. The sanitary clamp includes first and second semi-circular members which can be connected and locked together to form a circular aperture for receiving the funnel shaped ends of the pair of connectors. The first and second members also have second ends providing a locking device for selectively locking the first and second members together after the pair of barb connectors are disposed therein. In this example, the locking device includes a ratchet with external teeth. The ratchet is connected to the first member. The locking device also includes a housing extending from the second end of the second member. The housing is configured to receive the ratchet. The housing has side walls with a rocker lock formed therein for defining a path of movement for locking and unlocking the teeth of the ratchet within the housing.

Different examples of locking devices can include different mechanisms for engaging the ratchet and the housing. For example, pliers can be used to engage the ratchet and housing. In another example, a handle can have a cam portion for engaging the ratchet and housing by pulling the ratchet after the ratchet is inserted into the housing. In a third example, a handle is rotatable to pull the ratchet into engagement with the housing.

In another example of a sanitary clamp that does not include a ratchet, the sanitary clamp includes first and second semi-circular members that can be connected and locked together to form a circular aperture, and the first and second members also have second ends providing a locking device for selectively locking the first and second members together after the barb connectors are disposed therein. A pin is rotatably connected to the second end of the second member, and the pin can be rotated for insertion between a pair of arms defined by the second end of the first member. A handle threaded to the pin can be rotated to apply pressure to the first member, which in turn results in pressure between the first and second member that prevents movement of the first member relative to the second member.

BRIEF DESCRIPTION OF THE DRAWINGS

The description herein makes reference to the accompanying drawings wherein like reference numerals refer to like parts throughout the several views, and wherein.

DETAILED DESCRIPTION OF EMBODIMENTS OF THE INVENTION

Referring to FIGS. 1A to 3B, a first example of a sanitary clamp 10 is configured for connecting two sanitary connections 12 having funnel shaped ends. Each sanitary connection 12 includes a tubular member 13 having a barb connection 14 at one end for connection to a tube (not shown). Each sanitary connection 12 has an end opposite the barb connection 14 with a funnel formation 16 including an expanded circular opening at its terminating end 18.

Figure 1A:
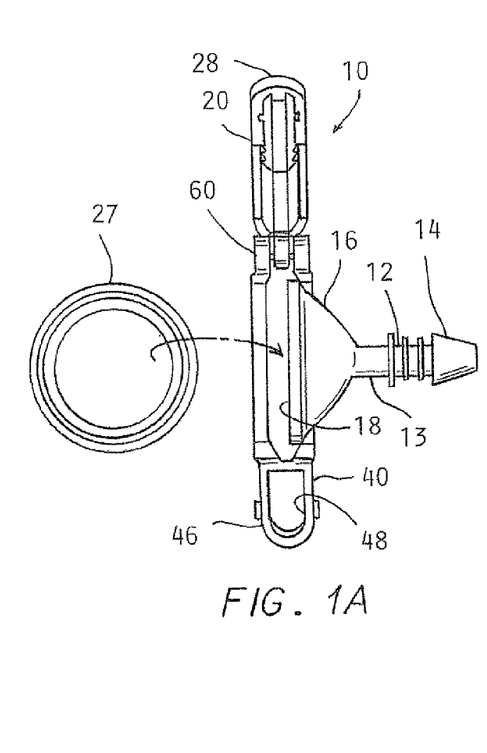
FIG. 1A is an elevational view of a sanitary assembly with one funnel shaped end of a barb connector disposed in and implementing an example of a sanitary clamp, the sanitary clamp having a first and second member.
Figure 1B:
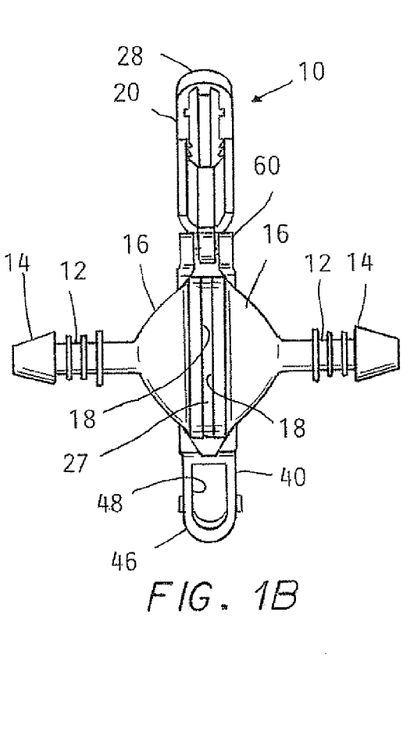
FIG. 1B is an elevational view of the sanitary assembly with an O-ring and pair of funnel shaped ends of barb connectors disposed in and implementing the sanitary clamp of FIG. 1A.
Figure 1C:
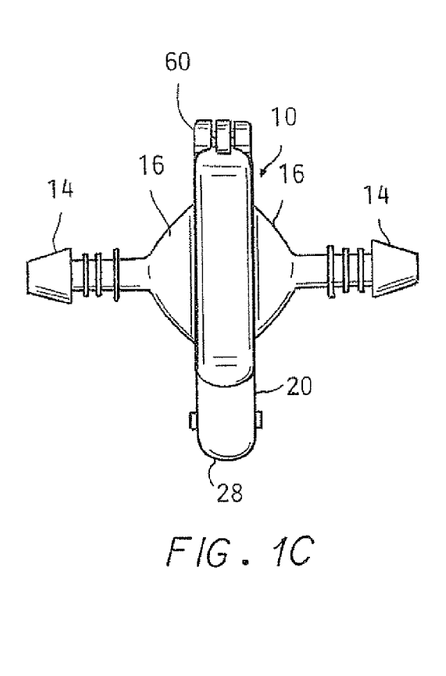
FIG. 1C is an elevational view of the sanitary assembly of FIG. 1B locked in the sanitary clamp.

The sanitary clamp 10, which can fluidly and sealingly connect the pair of sanitary connections 12, can be made of a high molecular weight thermoplastic polymer such as a polyvinylidene difluoride (PVDF) polymer sold under the name of Kynar, a registered trademark of Elf Atochem North America, Inc. Kynar is generally suitable for use in applications requiring high purity, strength, and resistance of solvents, acids, bases and heat. As an alternative, a polysulfone (PSU) can also be used to make the sanitary clamp 10.

Figures 2A, 2B:
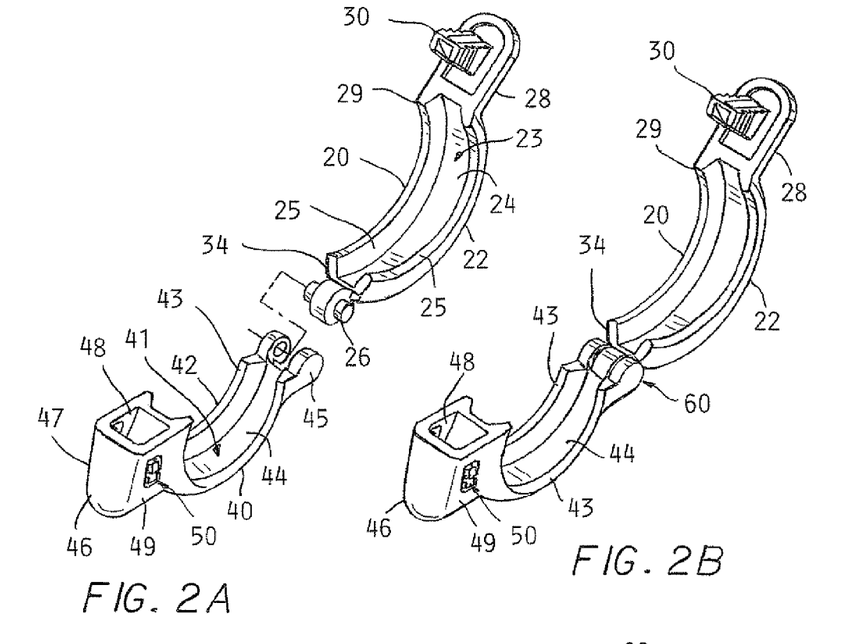
FIG. 2A an exploded view of the sanitary clamp of FIG. 1.
FIG. 2B is a perspective view of the sanitary clamp of FIG. 2A connected at a hinge.

The sanitary clamp 10 is formed by first and second semi-circular members 20 and 40, respectively connected together at a hinge 60. The first member 20 has an arcuate, semi-circular portion 22 with an interior groove 24 formed between a pair of parallel side walls 25 and an interior surface of the circular portion 22. The interior groove 24 is sized and configured for receiving semi-circular portions of the terminating ends 18 of the funnel formations 16 of the pair of sanitary connections 12 with an O-ring seal 27 therebetween. At one end 34 of the first member 20 adjacent to the semi-circular portion 22 is an extending tab 26 forming a male portion of the hinge 60. On an opposing end 29 of the first member 20 and attached to the semi-circular 22 portion is a ledge 28 which extends essentially perpendicular from the end 29 of the semi-circular portion 22. The inner surface of the ledge 28 carries a ratchet 30 with external teeth 32 along opposing sides of the ratchet 30.

The second member 40 of the sanitary clamp 10 has a center semi-circular portion 42 forming an inner groove 44 between its internal surface 41 and a pair of parallel side walls 43. The inner groove 44 is configured for receiving the O-ring seal 27 disposed between the pair of terminating ends 18 of the sanitary connections 12. The second member 40 has one bifurcated end 45 forming a female portion of the hinge 60. The first and second members 20 and 40 are connected together at their ends 34 and 45 to form the hinge 60. The hinge 60 is formed for connection of the extending tab 26 of the first member 20 to the bifurcated end 45 of the second member 40 to allow the clamp 10 to rotate in place similar to a conventional metal clamp. The hinge 60 is configured to be positioned on the outside surfaces of the first and second members 20, 40 so as not to interfere with the disposition of the sanitary connectors 12 within the clamp 10.

The second member 40 has a housing 46 extending from an end 47 opposite the end 45 and spaced from the hinge portion 60. The housing 46 forms a well 48 therein for receiving the ratchet 30 of the first member 20. The housing 46 of the second member 40 has opposing sidewalls 49. The sidewalls 49 are mirror images of each other and therefore only one sidewall 49 will be discussed. In a center portion of the sidewall 49, a rocker lock 50 is formed therein. The rocker lock 50 is cut directly into each sidewall 49 leaving a gap/opening 51 around the rocker lock 50 except for connecting flanges 53 which connect a mid-section of the rocker lock 50 to the material of the sidewalls 49. The rocker lock 50 pivots about the connecting flanges 53. Manual pressure on either a lower end 50*a* or an upper end 50*b* of the rocker lock 50 will cause the opposite end 50*b* or 50*a*, respectively, of the rocker lock 50 to flex outward relative to the sidewalls 49. The gap/opening 51 is sized at the upper end 50*b* and lower end 50*a* of the rocker lock 50 to accommodate the teeth 32 on the ratchet 30 of the first member 20. The upper end 50*b* of the rocker lock 50 forms an outwardly extending button 52 to facilitate the manual depression of the upper end 50*b* of the rocker lock 50 to release the ratchet 30 from the housing 46.

Figure 2C:
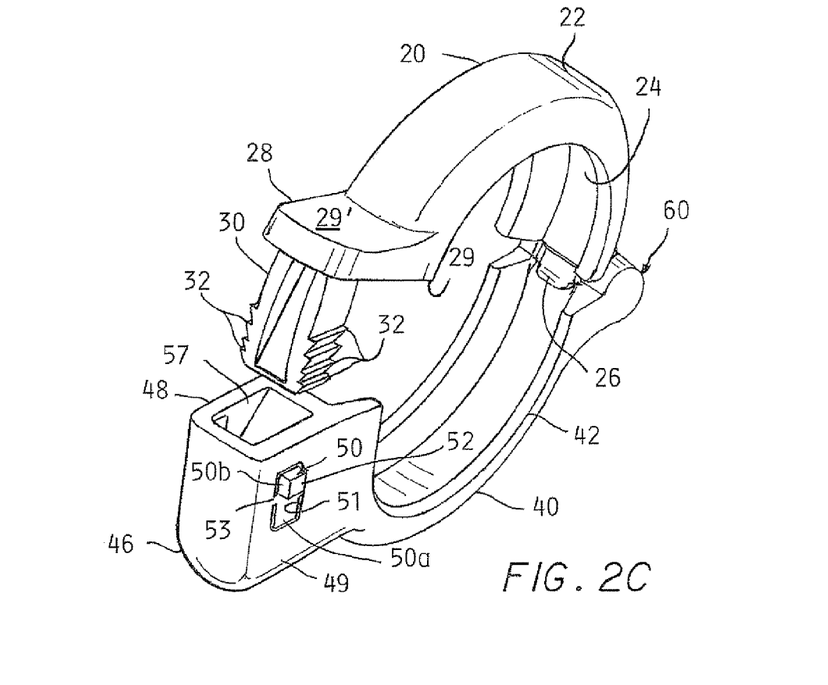
FIG. 2C is front perspective view of the sanitary clamp of FIG. 2B in a partially closed position.
Figure 3A:
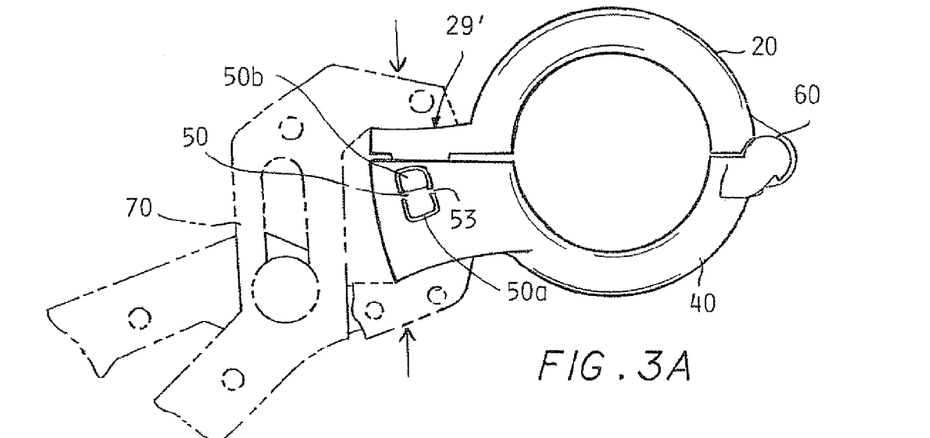
FIG. 3A is a side elevational view of the sanitary clamp of FIG. 1 with a locking device placed in the locked position by parallel closing pliers.
Figure 3B:
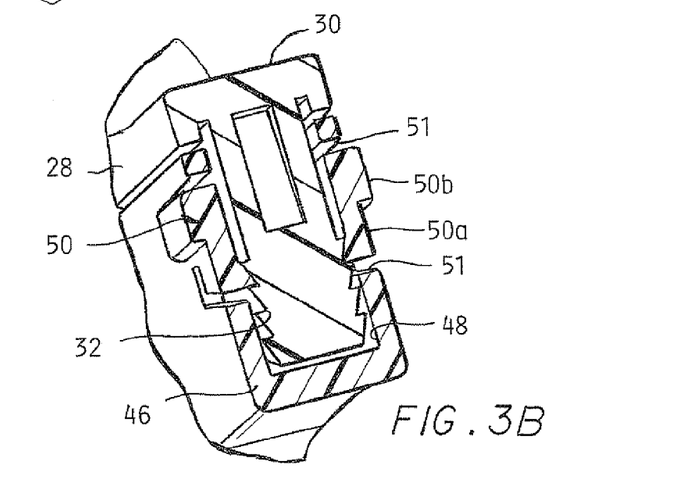
FIG. 3B is a sectional view of the locking device of FIG. 3A in a locked position.
Figure 4:
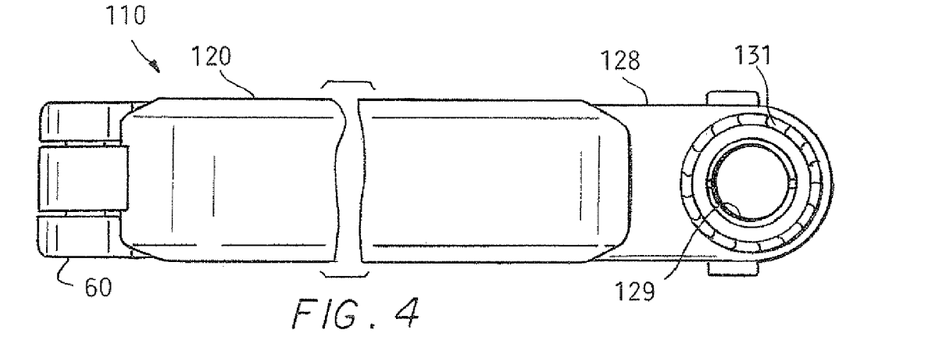
FIG. 4 is a top elevational view of a second example of a sanitary clamp.

As manual downward pressure is applied to the first member 20, the teeth 32 on the ratchet 30 slide along an inner surface 57 of the rocker lock 50 as can be understood from FIG. 2C. A pair of parallel closing pliers 70 as shown in FIG. 3A is used to complete the closure by depressing on an upper surface 29' of the ledge 28 and the housing 46 of the first and second members 20 and 40, respectively as illustrated by the arrows in FIG. 3. Once the teeth 32 are latched into the gaps 51 of the rocker locks 50, the teeth 32 cannot be released without depressing the buttons 52 of the rocker locks 50. To ensure a secure lock of the teeth 32 within the gaps 51, the teeth 32 are angled upward toward the ledge 28 of the first member 20 as shown in FIG. 2C to prevent easy pull out of the ratchet 30 from the housing 46.

Another example of a closure and locking mechanism as shown in FIGS. 4-6C can be provided for a disposable sanitary clamp 110. The sanitary clamp 110 is similar to the sanitary clamp 10, though the sanitary clamp 110 includes a first member 120 instead of the first member 20 of the sanitary clamp 10. The first member 120 of the sanitary clamp 110 includes a through aperture 129 through its ledge 128. The aperture 129 is surrounded by a ribbed peripheral upper edge 131. The ribs on the upper edge 131 are spaced at, for example, 10° intervals. The second member 40 is unchanged.

Figures 5A, 5B, 5C:
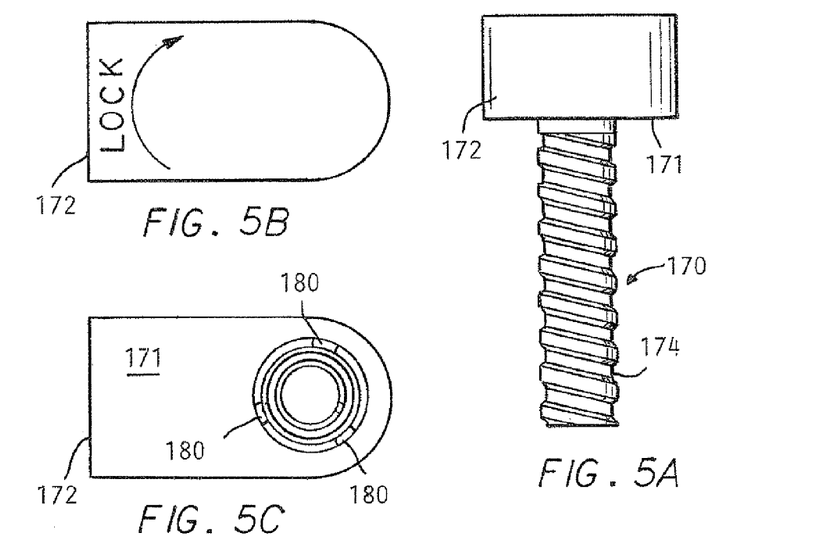
FIG. 5A is an elevational view of a locking knob of the sanitary clamp according to the second example, the locking knob having a handle and acme thread.
FIG. 5B is a top view of the locking knob showing a top surface of the handle.
FIG. 5C is a bottom view of the locking knob.

The through aperture 129 is configured for receiving a locking knob 170 having a handle portion 172 integrally connected to an acme thread 174 extending from a bottom surface 171 of the handles 122. A ratchet 130 of the second example has a center cavity 176 for receiving the acme thread 174. The acme thread 174 is configured to be inserted within the central cavity 176 of the ratchet member 130. The ratchet member 130 may be connected along its upper edge 133 to the bottom surface of the ledge 128. Alternatively, the ratchet member 130 can be a separate member initially separate from the ledge 128 and first member 120. In the alternative, the ratchet 130 is inserted into the well 48 of the housing 46 and then secured in place with the locking knob 170. The locking knob 170 functions to fully tighten the assembly beyond finger tight as would be done in the first embodiment by the pliers 70.

Figures 6A, 6B:
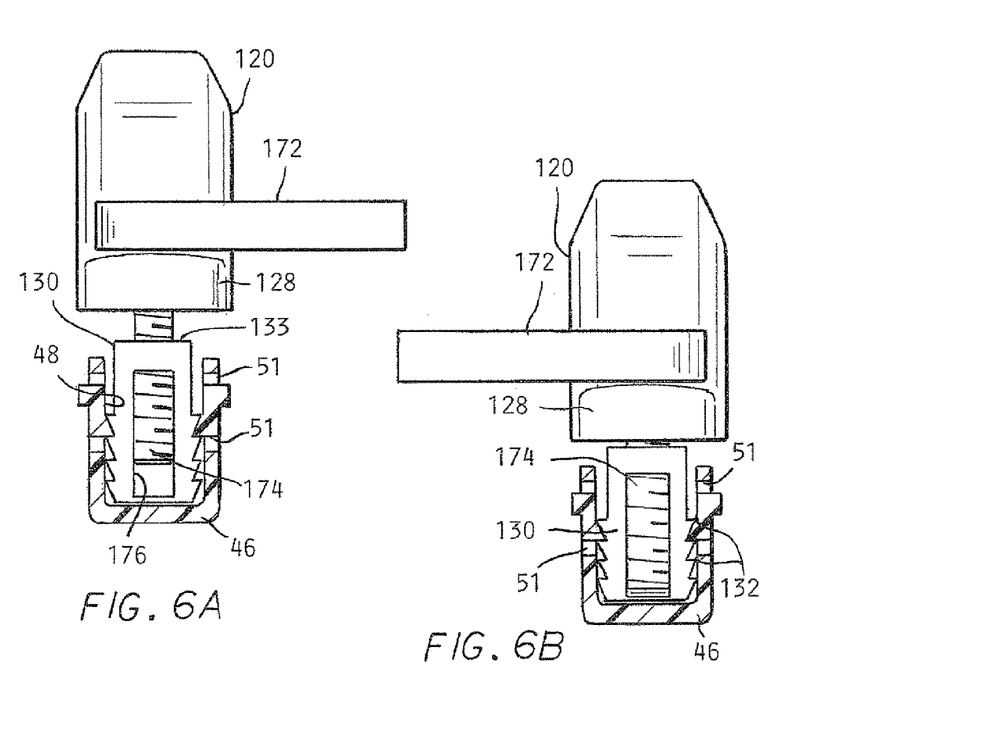
FIG. 6A is a partial sectional view of the locking knob installed in a ratchet and a first member of the sanitary clamp in an unlocked position.
FIG. 6B is a partial sectional view of the locking knob in a locked position.

When the ratchet 130 having the acme thread 174 installed therein is positioned and manually pressured into connection with the well 48 of the second member 40, the handle portion 172 can then be moved clockwise so that the acme thread 174 pulls the ratchet 130 and its associated teeth 132 toward the rocker locks 50 for locking the teeth 132 into the gaps 51 and thereby tightening the assembly beyond finger tight. FIG. 6A shows the closure in an unlocked position. FIG. 6B shows the closure in a locked position. When the closure is in a locked position, the housing 46 of the second member 40 is drawn up to the ledge 128 of the first member 120. The locked position of the handle 172 can be any point between 0 and 180 degrees in increments of 10 degrees from the unlocked position via the ribbed upper edge 131 of the aperture 129 of the upper member 120. Integrally formed ratchet teeth 180 shown in FIG. 5B on the bottom surface 171 of the handle 172 of the locking knob 170 cooperating with the ribbed upper edge 131 of the first member 120 will prevent the handle 172 from becoming unlocked on its own.

Figure 7:
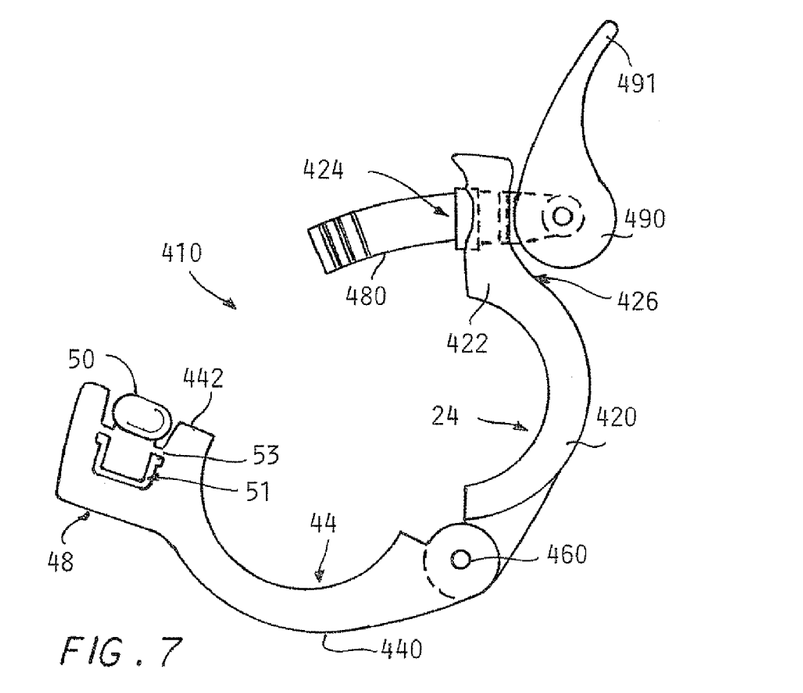
FIG. 7 is a side elevation view of a third example of a sanitary clamp.

A third example of a sanitary clamp 410 shown in FIG. 7 can include a first member 420 and a second member 440 rotatably coupled to one another at a hinge 460. The first and second members 420 and 440 can define the grooves 24 and 44 for receiving the terminating ends 18 of the sanitary connections 12. An end 422 of the first member 420 opposite the hinge 460 can define an aperture 424 and a curved cam receiving surface 426. A pin 480 shown in FIG. 8 can have a first end 482 that is sized to fit through the aperture 424 defined by the first member 420, and the first end 482 of the pin 480 can define an aperture 484. A stop 486 defined by the pin 480 can be spaced from the first end 482, and the stop 486 can have a larger size than at least a portion of the aperture 424 defined by the first member 420 such that movement of the pin 480 through the aperture 424 is limited due to contact between the stop 486 and the first member 420. A second end 488 end of the pin 480 opposite the first end 482 can function as a ratchet, i.e., opposing sides of the second end 488 can define a plurality of teeth 489.

Figures 8, 9, 10, 11:
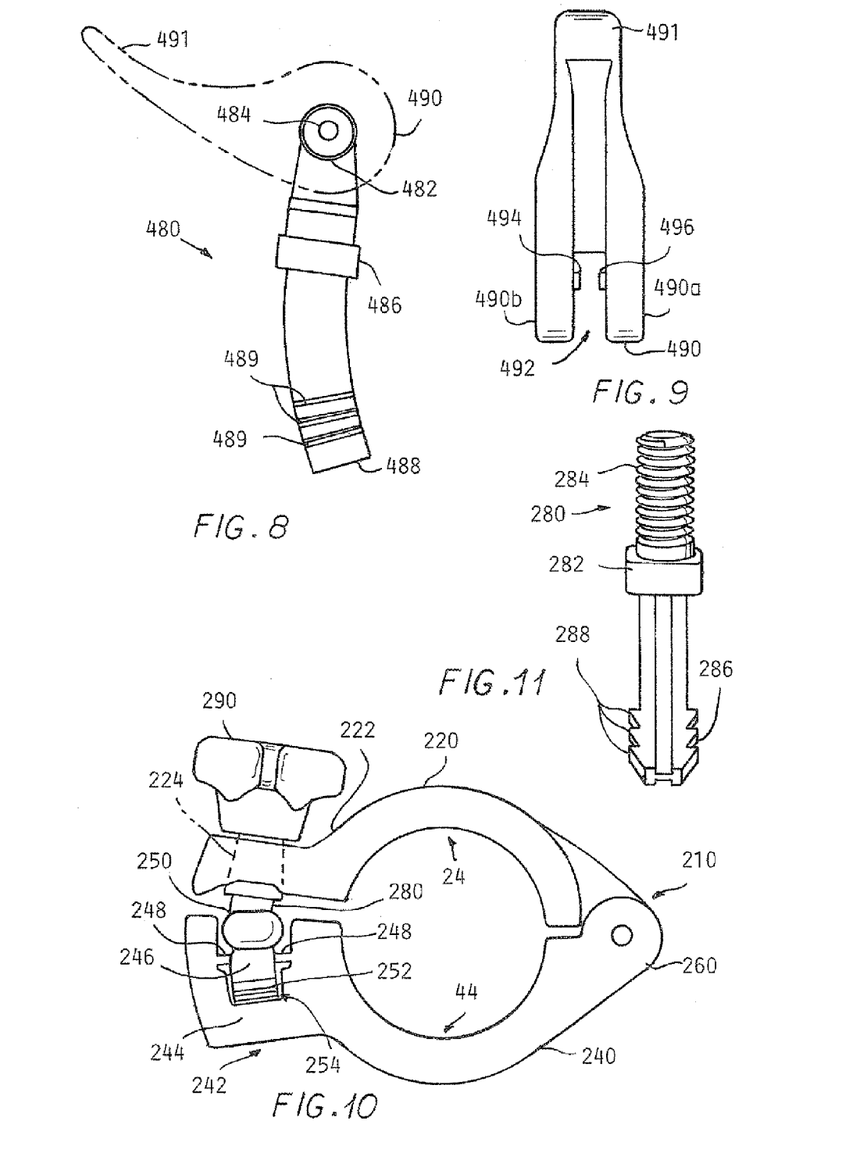
FIG. 8 is a side elevation view of a pin for the third example of the sanitary clamp including a handle in phantom.
FIG. 9 is a rear end elevation view of the handle of FIG. 8.
FIG. 10 is a side elevation view of a fourth example of a sanitary clamp.
FIG. 11 is a perspective view of a pin for the fourth example of the sanitary clamp.

The sanitary clamp 410 can also include a handle 491 having a cam portion 490. The cam portion 490 can include a pair of parallel sidewalls 490a and 490b defining a groove 492 as shown in FIG. 9, and the handle 491 can also define a pair of pins 494 and 496 extending toward one another within the groove 492. The groove 492 can extend circumferentially relative to an axis defined by the pins 494 and 496.

After inserting the first end 482 of the pin 480 through the aperture 424 in the first member 420, the first end 482 of the pin 480 can be inserted into the groove 492 to engage the pins 494 and 496 of the handle 491 with the aperture 484 defined by the pin 480, thereby rotatably coupling the handle 491 and pin 480.

With the handle 491 rotatably coupled to the pin 480, rotation of the handle 491 can cause engagement of the cam portion 490 of the handle 491 with the cam receiving surface 426 of the first member 420. As a result of this engagement, rotation of the handle 491 can move the pins 494 and 496 away from the cam receiving surface 426, which in turn can move the pin 480 such that its stop 486 and teeth 489 move toward the aperture 424 defined by the first member 420.

An end 442 of the second member 440 spaced from the hinge 460 can include the well 48 having the rocker locks 50 and gaps 51, and the rocker locks 50 can be attached to the well 48 via the connecting flanges 53.

With the first and second members 420 and 440 rotated apart from one another, the terminating ends 18 of the sanitary connections 12 and the O-ring seal 27 can be inserted into the groove 44 in the second member 440. With the handle 491 in an inactivated position as shown in FIG. 8, the first and second members 420 and 440 can be rotated toward one another such that the pin 480 is inserted into the well 48 and the ends 422 and 442 of the first and second members 420 and 440, respectively, are in contact with or closely spaced from one another. Rotation of the first and second members 420 and 440, respectively, toward one another can cause the first member 420 to engage the terminating ends 18 of the sanitary connections 12 and the O-ring seal 27. The handle 491 can be rotated to engage its cam portion 490 with the cam receiving surface 426 of the first member 420 as described above, thereby pulling the pin 480 in a direction out of the well 48. In response to the pin 480 being pulled in a direction out of the well 48, the teeth 489 on the pin 480 can engage the gaps 51 in the well 48, thereby limiting the movement of the pin 480 relative to the well 48 and locking the first and second members 420 and 440, respectively, in an engaged position in which the sanitary clamp 410 fluidly couples the sanitary connections 12.

Also, the illustrated sanitary clamps 10, 110 and 410 can have different configurations from as shown without altering their respective functions. For example, a sanitary clamp 210 shown in FIG. 10 functions in essentially the same manner as the sanitary clamp 110 shown in FIGS. 4-6C. The sanitary clamp 210 includes first and second members 220 and 240, respectively, rotatably coupled at a hinge 260 and defining the grooves 24 and 44 for receiving the terminating ends 18 of the sanitary connections 12 and the O-ring seal 27. An end 222 of the first member 220 opposite the hinge 260 defines an aperture 224, and a pin 280 is inserted through the aperture 224. The pin 280, which is shown in FIG. 11, includes a stop 282 that can contact the first member 220 to limit movement of the pin 280 through the aperture 224 in the first member 220, and the pin 280 also includes a threaded end 284 and a ratchet end 286 opposite the threaded end 284. Two opposing sides of the ratchet end 286 of the pin 280 each include a plurality of teeth 288. A plus-sign shaped handle 290 can be threaded onto the threaded end 284 of the pin 280.

The second member 240 can define a through-bore 242. Opposing sidewalls 244 partially defining the bore 242 can each include a rocker lock 246 coupled to its sidewall 244 by a pair of connecting flanges 248. The rocker lock 246 can include a button 250 that can be urged inward toward the opposing sidewall 244 to move a lower end 252 of the rocker lock 246 outward away from the opposing sidewall 244. A gap 254 can be defined between the lower end 252 of the rocker lock 246 and the sidewall 244.

The terminating ends 18 of the sanitary connections 12 can be inserted into the groove 44 in the second member 240 with the second member 240 and first member 220 rotated away from each other. The first member 220 can be rotated toward the second member 240 to insert the pin 280 into the well 242. The handle 290 can be rotated about the threaded portion 284 of the pin 280, which in turn pulls the pin 280 in a direction outward from the well 242 toward the handle 290. Movement of the pin 280 in the direction outward from the well 242 can be prevented via engagement between the teeth 289 on the ratchet end 286 of the pin 280 and the gaps 254 defined by the well 242. The engagement between the teeth 289 and the well 242 can prevent movement of the first member 220 relative to the second member 240, thereby securing the sanitary clamp 210 in a closed position.

Despite their similar functions, the sanitary clamp 210 has several differences compared to the sanitary clamp 110. The sidewalls 244 of the sanitary clamp 210 do not span an upper portion of the rocker lock 246, which allows the button 250 to be larger. The pin 280 is an integral member including both the threaded and ratchet ends 284 and 286, thereby reducing the number of parts. The shape of the handle 290 is a plus sign, which enables easy gripping of the handle 290.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed:

1. A sanitary clamp for connection to a pair of barb connectors each having one end terminating at a funnel shaped portion, the sanitary clamp comprising:
   a first member having a first semi-circular center portion disposed between a first end and a second end; and a second member having a second semi-circular center portion disposed between a first end and a second end, said first ends of the first and second members configured to pivotally connect to each other such that said first and second members are pivotable to form an aperture configured to receive the funnel shaped portions of the pair of connectors and maintain the funnel shaped portions in a fluid tight relationship, said second ends of the first and second members including a locking mechanism for selectively locking the second ends of the first and second members in engagement, wherein the locking mechanism includes a pin, a ledge extending from the second end of the first semi-circular portion, and a housing extending from the second end of the second semi-circular portion, and wherein the ledge defines an aperture, wherein the pin passes through the aperture and includes a ratchet having a plurality of ratchet teeth and a handle operable to urge the ratchet toward the handle, and wherein the housing defines a well configured for receiving and releasably locking the ratchet and includes two opposed walls each having a rocker lock with a first portion, an opposed second portion including an engaging member and a flange therebetween pivotally connecting the rocker lock to its respective wall such that the second portion travels outwardly when the first portion is inwardly depressed, wherein the rocker lock is configured to resiliently position the engaging member in the well to engage the at least one external ratchet tooth and is configured to permit retraction of the engaging member with respect to the well to release the engaging member from engagement with the at least one external ratchet tooth in response to depression of the first portion.

2. The sanitary clamp of claim 1, wherein the ledge extends orthogonally from the first semi-circular portion.

3. The sanitary clamp of claim 1, wherein the ratchet has side walls having the plurality of external ratchet teeth, said teeth disposed on the side walls of the ratchet.

4. The sanitary clamp of claim 3, wherein the teeth are angled upward toward a bottom surface of the ledge.

5. The sanitary clamp of claim 1, wherein the ratchet and the handle are on opposing sides of the ledge from each other.

6. The sanitary clamp of claim 5, wherein a stop is disposed on the pin between the ratchet and the ledge, and wherein the stop is operable to limit movement of the pin relative to the ledge.

7. The sanitary clamp of claim 1, wherein the ratchet is disposed at an end of the pin opposite the handle.

8. The sanitary clamp of claim 1, wherein the handle is rotatable about an axis defined by the pin, and wherein a threaded engagement is operable to urge the ratchet toward the handle in response to rotation of the handle.

9. The sanitary clamp of claim 8, wherein one end of the pin defines the ratchet and an opposing end of the pin defines a threaded portion, and wherein the threaded engagement includes engagement of threaded portion of the pin with a cavity defined by the handle.

10. The sanitary clamp of claim 1, wherein a hinge rotatably couples the pin and the handle.

11. The sanitary clamp of claim 10, wherein the handle defines a cam and the first member defines a cam receiver, and the cam of the handle is operable to contact the cam receiver of the first member in response to rotation of the handle about an axis defined by the hinge.

12. The sanitary clamp of claim 11, wherein an end of the pin opposite the handle defines the ratchet.

13. The sanitary clamp of claim 11, wherein the cam of the handle includes two spaced sidewalls, and wherein the pin is rotatably coupled to the cam between the two spaced sidewalls.

14. A polymeric clamp for releasably connecting terminating ends of a pair of sanitary connectors, comprising:

a first member connected to a second member by a pivot connection at a first end of each of the first and second members allowing for pivoting of the first member relative to the second member between an open position and a closed position, the first and second members spaced apart to receive the terminating ends in the open position and configured to retain the terminating ends in a fluid tight relationship in the closed position;

a locking device for releasably locking second ends of the first and second members in the closed position, the locking device including a projection having a plurality of external ratchet teeth coupled to the second end of the first member and a housing defining a well on the second end of the second member configured for receiving the projection, wherein the second member includes a rocker lock with a first portion, an opposed second portion including an engaging member and a flange therebetween pivotally connecting the rocker lock to the second member such that the second portion travels outwardly when the first portion is inwardly depressed, wherein the rocker lock is configured to resiliently position the engaging member in the well to engage the at least one external ratchet tooth to latch the projection within the well and is configured to permit retraction of the engaging member with respect to the well to release the engaging member out of engagement with the at least one external ratchet tooth in response to depression of the first portion to unlatch the projection from the well; and closure means connected to the second end of the first member for drawing the first and second members to the closed position when the projection is latched within the housing.

15. The clamp of claim 14, wherein the closure means comprises:

an aperture defined by a ledge included in the first member;

a pin having a threaded end opposing the projection, the pin extending through the aperture to couple the projection to the first member such that the threaded end and the projection are disposed on opposing sides of the ledge; and a handle threadedly engaged with the threaded end of the pin such that the handle is operable to be urged toward the projection when rotated about the threaded end of the pin, wherein the handle is configured to engage the ledge while rotating to urge the ledge towards the housing to draw the first and second members to the closed position when the projection is latched within the well.

16. The clamp of claim 15, wherein a stop is disposed on the pin between the projection and the ledge to limit movement of the pin relative to the ledge.

17. The clamp of claim 14, wherein the first and second members define a continuous annular groove in the closed position for retaining the terminating ends in a fluid tight relationship.

18. The clamp of claim 17, wherein the annular groove is at least partially defined by a pair of opposing side walls configured to retain the terminating ends in a fluid tight relationship by engaging respective flanges included in the terminating ends.

19. The clamp of claim 17, wherein the annular groove is configured to receive an O-ring disposed between the terminating ends.

20. The clamp of claim 14, wherein the closure means comprises:
   an aperture defined by a ledge included in the first member;
   a pin having a handle opposing the projection, the pin extending through the aperture to couple the projection to the first member such that the handle and the projection are disposed on opposing sides of the ledge; and
   wherein a hinge rotatably couples the pin and the handle.

21. The clamp of claim 20, wherein the handle defines a cam and the first member defines a cam receiver, and the cam of the handle is operable to contact the cam receiver of the first member in response to rotation of the handle about an axis defined by the hinge.

22. A sanitary assembly, comprising:
   a pair of tubular barb connectors each having an open funnel shaped terminating end, wherein the terminating ends are opposedly positionable to define a continuous passage through the connectors;
   a clamp composed of a thermoplastic polymer and configured to sealingly connect the terminating ends of the connectors such that the passage is fluid tight; and
   the clamp having a first member, a second member pivotally connected at a first end of each of the first and second members and a locking mechanism located at second ends of each of the first and second members; wherein:
      the first and second members are pivotable relative to one other between an open position and a closed position, the first and second members configured to sealingly connect the terminating ends in the closed position,
      the locking and closure mechanism is configured for locking the first and second members in the closed position, the locking and closure mechanism including a ratchet having a plurality of external ratchet teeth coupled to the second end of the first member; and a housing defining a well on the second end of the second member configured for receiving the ratchet, wherein the second member includes a rocker lock with a first portion, an opposed second portion including an engaging member and a flange therebetween pivotally connecting the rocker lock to the second member such that the second portion travels outwardly when the first portion is inwardly depressed, wherein the rocker lock is configured to resiliently position the engaging member in the well to engage the at least one external ratchet tooth to latch the ratchet within the well and is configured to permit retraction of the engaging member with respect to the well to release the engaging member out of engagement with the at least one external ratchet tooth in response to depression of the first portion to unlatch the ratchet from the well, and
      the locking and closure mechanism is further configured for drawing the first and second members to the closed position when the ratchet is latched within the housing, the locking and closure mechanism including an aperture defined by a ledge disposed on the second end of the first member, a pin having a threaded end opposing a ratchet end integrally forming the ratchet, the pin extending through the aperture to couple the ratchet to the first member such that the threaded end and the ratchet are disposed on opposing sides of the ledge, and a handle threadedly engaged with the threaded end of the pin such that the handle is operable to be urged toward the ratchet when rotated about the threaded end of the pin, wherein the handle is configured to engage the ledge while rotating to urge the ledge towards the housing to draw the first and second members to the closed position when the ratchet is latched within the well.

23. The clamp of claim 22, wherein the first and second members define a continuous annular groove in the closed position for retaining the terminating ends in a fluid tight relationship.

* * * * *